US012573504B2

(12) United States Patent
Im et al.

(10) Patent No.: US 12,573,504 B2
(45) Date of Patent: Mar. 10, 2026

(54) APPARATUS FOR DIAGNOSING DISEASE CAUSING VOICE AND SWALLOWING DISORDERS AND METHOD FOR DIAGNOSING SAME

(71) Applicants: THE CATHOLIC UNIVERSITY OF KOREA INDUSTRY-ACADEMIC COOPERATION FOUNDATION, Seoul (KR); POSTECH RESEARCH AND BUSINESS DEVELOPMENT FOUNDATION, Pohang-si (KR)

(72) Inventors: Sun Im, Seoul (KR); Seungchul Lee, Pohang-si (KR); Juhyeong Jeon, Pohang-si (KR); Young Hoon Joo, Seoul (KR); Yeon Jae Han, Seoul (KR)

(73) Assignees: THE CATHOLIC UNIVERSITY OF KOREA INDUSTRY-ACADEMIC COOPERATION FOUNDATION, Seoul (KR); POSTECH RESEARCH AND BUSINESS DEVELOPMENT FOUNDATION, Pohang-si (KR)

( * ) Notice: Subject to any disclaimer, the term of this patent is extended or adjusted under 35 U.S.C. 154(b) by 459 days.

(21) Appl. No.: 17/908,629

(22) PCT Filed: Mar. 4, 2021

(86) PCT No.: PCT/KR2021/002651
§ 371 (c)(1),
(2) Date: Sep. 1, 2022

(87) PCT Pub. No.: WO2021/177730
PCT Pub. Date: Sep. 10, 2021

(65) Prior Publication Data
US 2023/0130676 A1 Apr. 27, 2023

(30) Foreign Application Priority Data
Mar. 5, 2020 (KR) ........................ 10-2020-0027690

(51) Int. Cl.
*G16H 50/20* (2018.01)

(52) U.S. Cl.
CPC ................................... *G16H 50/20* (2018.01)

(58) Field of Classification Search
CPC .................................................... G16H 50/20
See application file for complete search history.

(56) References Cited

U.S. PATENT DOCUMENTS

| | | | |
|---|---|---|---|
| 9,579,056 B2* | 2/2017 | Rosenbek | A61B 5/7275 |
| 2019/0088367 A1* | 3/2019 | Stamatopoulos | G16H 50/20 |
| 2019/0189146 A1* | 6/2019 | Levanon | G10L 25/12 |

FOREIGN PATENT DOCUMENTS

| | | | |
|---|---|---|---|
| CN | 109431507 A | 3/2019 | |
| CN | 109584861 A * | 4/2019 | G10L 15/063 |

(Continued)

OTHER PUBLICATIONS

KR20170045798A—translated (Year: 2017).*

(Continued)

*Primary Examiner* — Jason S Tiedeman
*Assistant Examiner* — Jonathan C Edouard
(74) *Attorney, Agent, or Firm* — Harness, Dickey & Pierce, P.L.C.

(57) ABSTRACT

An apparatus for diagnosing a disease and a method for diagnosing a disease, in which: a plurality of voice signals are received to generate a first image signal and a second image signal which are image signals for each voice signal; a plurality of disease probability information for a target disease causing a voice change are extracted by using an artificial intelligence model determined according to the type of each voice signal and a generation method used to generate each image signal for the first image signal and the second image signal for each voice signal; and it is deter- (Continued)

mined whether the target disease is negative or positive on the basis of the plurality of disease probability information.

5 Claims, 11 Drawing Sheets

(56)                    References Cited

FOREIGN PATENT DOCUMENTS

| | | | | | | |
|---|---|---|---|---|---|---|
| CN | 109599129 | A | * | 4/2019 | ............ | G10L 15/02 |
| KR | 20170045798 | A | * | 4/2017 | | |
| KR | 101936302 | B1 | * | 1/2019 | | |
| KR | 20190000194 | A | | 1/2019 | | |
| KR | 20190022151 | A | | 3/2019 | | |
| KR | 20190084460 | A | | 7/2019 | | |
| KR | 102015473 | B1 | | 8/2019 | | |
| KR | 102216160 | B1 | | 2/2021 | | |
| WO | 2014/178749 | A1 | | 11/2014 | | |
| WO | WO-2019083351 | A2 | * | 5/2019 | ........... | G06N 3/0454 |

OTHER PUBLICATIONS

Carvalho, Raphael Torres Santos, et al. "Wavelet Transform and Artificial Neural Networks Applied to Voice Disorders Identification." 2011 Third World Congress on Nature and Biologically Inspired Computing, 2011, pp. 371-376. IEEE Xplore, https://doi.org/10.1109/NaBIC.2011.6089256. (Year: 2011).*
International Search Report (English and Korean) and Written Opinion of the ISA (Korean) issued in PCT/KR2021/002651, mailed Jun. 17, 2021; ISA/KR.

* cited by examiner

Mel-frequency Filter Banks

* P<0.5 : negative   P>=0.5 : positive

FIG.8

|  | # of positive | # of negative | first result value |
|---|---|---|---|
| Case1-1 | 6 | 2 | positive |
| Case1-2 | 4 | 4 | positive |
| Case1-3 | 3 | 5 | negative |

FIG.9

Example1

| | # of positive | # of negative | $C_P$ | $C_N$ | first result value | second result value | whether there is disease |
|---|---|---|---|---|---|---|---|
| Case2-1 | 6 | 2 | 0.8 | 0.6 | positive | positive | positive |
| Case2-2 | 4 | 4 | 0.6 | 0.7 | positive | negative | positive |
| Case2-3 | 3 | 5 | 0.7 | 0.6 | negative | positive | positive |
| Case2-4 | 3 | 5 | 0.6 | 0.7 | negative | negative | negative |

FIG.10

Example2

| | # of positive | # of negative | $C_P$ | $C_N$ | first result value | second result value | whether there is disease |
|---|---|---|---|---|---|---|---|
| Case2-1 | 6 | 2 | 0.8 | 0.6 | positive | positive | positive |
| Case2-2 | 4 | 4 | 0.6 | 0.7 | positive | negative | negative |
| Case2-3 | 3 | 5 | 0.7 | 0.6 | negative | positive | positive |
| Case2-4 | 3 | 5 | 0.6 | 0.7 | negative | negative | negative |

APPARATUS FOR DIAGNOSING DISEASE CAUSING VOICE AND SWALLOWING DISORDERS AND METHOD FOR DIAGNOSING SAME

CROSS-REFERENCE TO RELATED APPLICATIONS

The instant patent application is a U.S. National Phase Application under 35 U.S.C. 371 of International Application No. PCT/KR2021/002651, filed on Mar. 4, 2021, which claims the benefit of Korean Patent Application No. 10-2020-0027690, filed on Mar. 5, 2020. The entire disclosures of the above applications are herein incorporated by reference in their entireties. The present patent application claims priority to other applications to be filed in other countries, the disclosures of which are also incorporated by reference herein in their entireties.

TECHNICAL FIELD

The present invention provides a device for diagnosing a disease causing speech and swallowing disorders and a method for diagnosing the same.

BACKGROUND ART

With the development of speech recognition technology, a technology for collecting health information about a patient, diagnosing a disease, and studying the reaction of a treatment agent using a voice signal in medicine and health care fields is being developed.

In the current medical and health care fields, the parameters mainly used to diagnose a patient's disease through a voice signal are fundamental frequency perturbation, amplitude perturbation, and signal to noise ratios.

However, to select these parameters from the voice signal, specialized equipment and skills are required, and it is difficult to analyze these parameters within a short time after receiving the voice signal in the medical site. Further, a model for diagnosing a patient's disease (e.g., Gaussian mixture model, support vector machine model) based on these parameters has disadvantages in that accuracy is low and it takes a long time to diagnose a patient's disease.

DETAILED DESCRIPTION OF THE INVENTION

Technical Problem

The embodiments provide a disease diagnosis device and a disease diagnosis method capable of rapidly diagnosing whether a disease accompanying speech and swallowing disorders is negative or positive.

Further, the embodiments provide a disease diagnosis device and a disease diagnosis method capable of reducing costs for treating diseases accompanying speech and swallowing disorders.

However, the objects of the embodiments are not limited thereto, and other objects may also be present.

Technical Solution

The disclosure discloses a disease diagnosis device and a disease diagnosis method that receive a plurality of voice signals and generate a first image signal and a second image signal that are image signals for each voice signal, extract a plurality of disease probability information for a target disease causing a voice change using an artificial intelligence model determined according to a type of each voice signal and a generation method used to generate each image signal for the first image signal and the second image signal for each voice signal, and determine whether the target disease is negative or positive based on the plurality of disease probability information.

An embodiment provides a disease diagnosis device comprising a pre-processing unit receiving a plurality of voice signals and generating a first image signal and a second image signal that are image signals for each voice signal, an extraction unit extracting a plurality of disease probability information for a target disease causing a voice change using an artificial intelligence model determined according to a type of each voice signal and a generation method used to generate each image signal for the first image signal and the second image signal for each voice signal, and a determining unit determining whether the target disease is negative or positive based on the plurality of disease probability information.

Another embodiment provides a disease diagnosis method comprising a pre-processing step receiving a plurality of voice signals and generating a first image signal and a second image signal that are image signals for each voice signal, an extraction step extracting a plurality of disease probability information for a target disease causing a voice change using an artificial intelligence model determined according to a type of each voice signal and a generation method used to generate each image signal for the first image signal and the second image signal for each voice signal, and a determining step determining whether the target disease is negative or positive based on the plurality of disease probability information.

Advantageous Effects

By the disease diagnosis device and disease diagnosis method according to embodiments, it is possible to quickly diagnose whether a disease accompanying speech and swallowing disorders is negative or positive.

Further, by the disease diagnosis device and disease diagnosis method according to embodiments, it is possible to reduce the cost of treating diseases accompanying speech and swallowing disorders.

BRIEF DESCRIPTION OF THE DRAWINGS

FIG. 8 is a view illustrating an example of a first result value according to the number of disease probability information determined as negative and disease probability information determined as positive;

FIG. 9 is a view illustrating an example in which a determining unit determines whether a target disease is negative or positive according to a first result value and a second result value;

FIG. 10 is a view illustrating another example in which a determining unit determines whether a target disease is negative or positive according to a first result value and a second result value.

DETAILED DESCRIPTION OF THE INVENTION

Hereinafter, exemplary embodiments of the inventive concept will be described in detail with reference to the accompanying drawings. The inventive concept, however, may be modified in various different ways, and should not be construed as limited to the embodiments set forth herein. Like reference denotations may be used to refer to the same or similar elements throughout the specification and the drawings. However, the present invention may be implemented in other various forms and is not limited to the embodiments set forth herein. For clarity of the disclosure, irrelevant parts are removed from the drawings, and similar reference denotations are used to refer to similar elements throughout the specification.

In embodiments of the present invention, when an element is "connected" with another element, the element may be "directly connected" with the other element, or the element may be "electrically connected" with the other element via an intervening element. When an element "comprises" or "includes" another element, the element may further include, but rather than excluding, the other element, and the terms "comprise" and "include" should be appreciated as not excluding the possibility of presence or adding one or more features, numbers, steps, operations, elements, parts, or combinations thereof.

When the measurement of an element is modified by the term "about" or "substantially," if a production or material tolerance is provided for the element, the term "about" or "substantially" is used to indicate that the element has the same or a close value to the measurement and is used for a better understanding of the present invention or for preventing any unscrupulous infringement of the disclosure where the exact or absolute numbers are mentioned. As used herein, "step of" A or "step A-ing" does not necessarily mean that the step is one for A.

As used herein, the term "part" may mean a unit or device implemented in hardware, software, or a combination thereof. One unit may be implemented with two or more hardware devices or components, or two or more units may be implemented in a single hardware device or component.

As used herein, some of the operations or functions described to be performed by a terminal or device may be, instead of the terminal or device, performed by a server connected with the terminal or device. Likewise, some of the operations or functions described to be performed by a server may be performed by a terminal or device connected with the server, instead of the server.

As used herein, some of the operations or functions described to be mapped or matched with a terminal may be interpreted as mapping or matching the unique number of the terminal, which is identification information about the terminal, or personal identification information.

Hereinafter, embodiments of the disclosure are described in detail with reference to the accompanying drawings.

Figure 1:
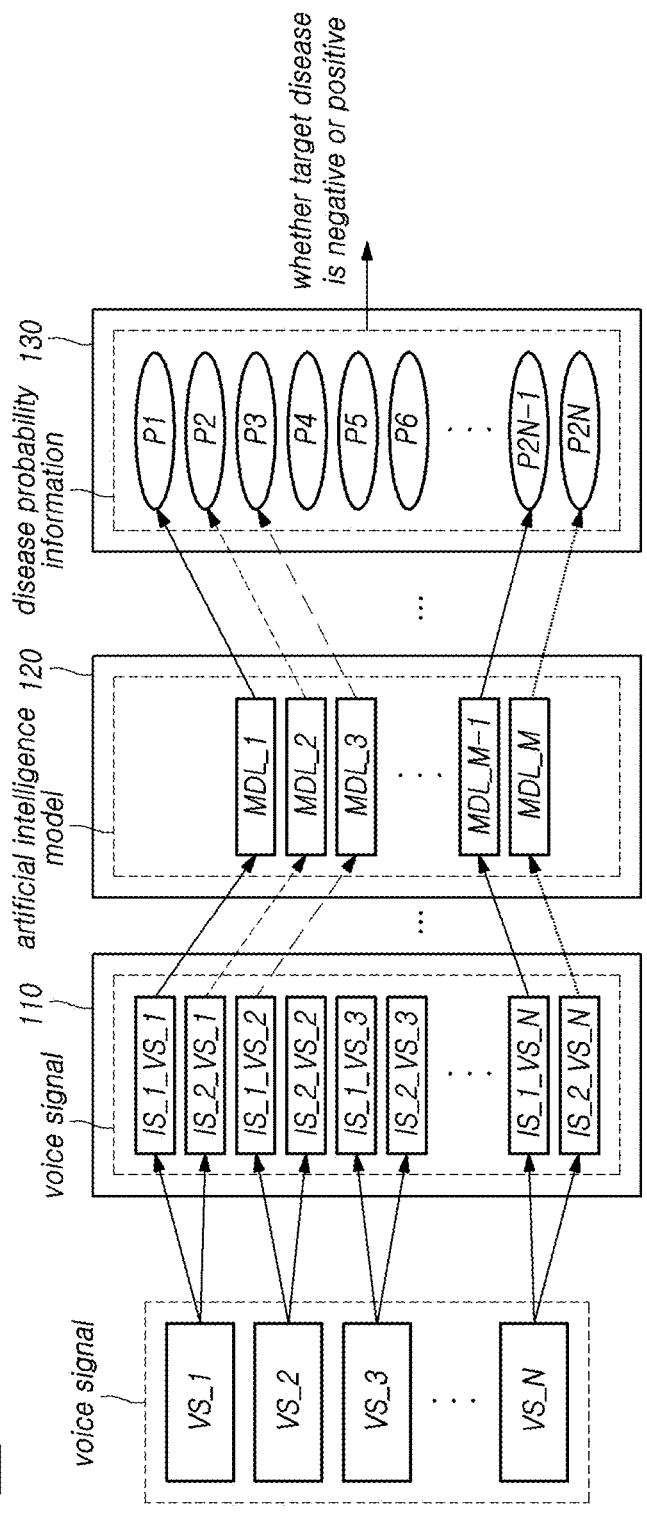
FIG. 1 is a block diagram illustrating a disease diagnosis device according to an embodiment.

FIG. 1 is a block diagram illustrating a disease diagnosis device according to an embodiment.

Referring to FIG. 1, a disease diagnosis device 100 may include a pre-processing unit 110, an extraction unit 120, and a determining unit 130.

The pre-processing unit 110 may receive a plurality of voice signals and generate a first image signal and a second image signal that are image signals for each voice signal.

In this case, the plurality of voice signals may be signals recorded from the patient through a device capable of recording voice (e.g., a smartphone, a tablet, a PDA, a digital camera, a smart watch, a digital/analog recorder). The format of the plurality of voice signals may be way, mp3, nsp, mp4, avi, etc., but is not limited to a specific format.

The first image signal and the second image signal for the voice signal are image signals obtained by converting the corresponding voice signal into an image form. A specific example of converting a voice signal into an image signal is described below in detail with reference to FIGS. 3 to 5.

It is assumed in FIG. 1 that the pre-processing unit 110 receives N (N is a natural number larger than or equal to 2) voice signals VS_1, VS_2, VS_3, . . . , VS_N.

The pre-processing unit 110 may generate a first image signal IS_1_VS_1 and a second image signal IS_2_VS_1 for the voice signal VS_1. Further, the pre-processing unit 110 may generate a first image signal IS_1_VS_2 and a second image signal IS_2_VS_2 for the voice signal VS_2. Further, the pre-processing unit 110 may generate a first image signal IS_1_VS_3 and a second image signal IS_2_VS_3 for the voice signal VS_3. In this manner, the pre-processing unit 110 may generate a first image signal IS_1_VS_N and a second image signal IS_2_VS_N for the voice signal VS_N.

The extraction unit 120 may extract a plurality of disease probability information for the target disease causing a voice change using an artificial intelligence model for the first image signal and the second image signal for each of the plurality of voice signals input to the pre-processing unit 110.

In this case, the artificial intelligence model may be determined according to the type of each voice signal and the generation method used to generate each image signal. The extraction unit 120 may use different artificial intelligence models for image signals generated from different types of voice signals and may use different artificial intelligence models even for the image signals generated from the same types of voice signals if the methods used to generate the image signals are different from each other. The reason why the extraction unit 120 uses different artificial intelligence models according to the type of each voice signal and the generation method used to generate each image signal is to prevent the artificial intelligence model from being over-optimized for a specific type of image or a specific image signal generation method when a single artificial intelligence model is used.

If each type of the plurality of voice signals is one of the K voice signal types, and the number of generation methods that may be used to generate each image signal is L, the extraction unit 120 may use K*L artificial intelligence models to extract a plurality of disease probability information. For example, if there are four types of voice signals and two generation methods may be used to generate an image signal, the number of artificial intelligence models that the extraction unit 120 may use is 4*2=8. A specific example of a type of each voice signal and a method for generating an image signal is described below with reference to the drawings.

In this case, the artificial intelligence model may be a machine learning model (e.g., decision tree, logistic regression analysis, support vector machine, random forest) or a deep learning model (e.g., CNN, RNN, GAN).

The target disease causing a voice change refers to a disease that may cause problems in the muscular nervous system (e.g., vocal cord muscles) positioned in the larynx of the patient due to dysphagia. For example, if a patient has laryngeal cancer, the voice the patient produces may be changed. As another example, if a patient has a stroke or dementia, dysphagia may change the voice the patient produces. The disease probability information about the target disease means the probability that the target disease occurs and may be a value between 0 and 1. Such a target disease may cause dysphagia in the patient and may cause a disorder in the patient's speech production through the vocal cords.

In FIG. 1, the pre-processing unit 110 may generate two image signals (a first image signal/second image signal) for each of the N voice signals, thereby generating a total of 2N image signals. The extraction unit 120 may extract 2N pieces of disease probability information about the target disease causing a voice change using any one of M different artificial intelligence models from the generated 2N image signals.

In FIG. 1, the extraction unit 120 may extract the disease probability information P1 using the artificial intelligence model MDL_1 for the first image signal IS_1_VS_1 for the voice signal VS_1. Further, the extraction unit 120 may extract the disease probability information P2 using the artificial intelligence model MDL_2 for the second image signal IS_2_VS_1 for the voice signal VS_1. Further, the extraction unit 120 may extract the disease probability information P3 using the artificial intelligence model MDL_3 for the first image signal IS_1_VS_2 for the voice signal VS_2. In this manner, the extraction unit 120 may extract the disease probability information P2N-1 using the artificial intelligence model MDL_M-1 for the first image signal IS_1_VS_N for the voice signal VS_N and may extract the disease probability information P2N using the artificial intelligence model MDL_M for the second image signal IS_2_VS_N for the voice signal VS_N.

The determining unit 130 may determine whether the above-described target disease is negative or positive based on the plurality of disease probability information extracted by the extraction unit 120. That the target disease is negative means that the number of pathogens causing the target disease is less than a reference value, i.e., a normal state, and that the target disease is positive means that the number of pathogens causing the target disease is larger than or equal to the reference value, i.e., an abnormal state.

A specific example in which the determining unit 130 determines whether the target disease is negative or positive is described below with reference to FIGS. 7 to 10.

According to the present embodiment, when the doctor uses the disease diagnosis device 100, the doctor may determine whether the target disease causing speech and swallowing disorders is negative or positive from the voice signal recorded from the patient without the need for the doctor to directly interview the patient, rendering it possible to quickly diagnose whether the disease accompanying speech and swallowing disorders is negative or positive. Further, if there is a device capable of recording voice, it is possible to record the patient's voice and determine whether the target disease causing voice and swallowing disorders is negative or positive. Thus, the cost of diagnosing a disease accompanying voice and swallowing disorders may be reduced.

Hereinafter, a specific embodiment of the operation of the disease diagnosis device 100 described with reference to FIG. 1 is described.

First, an example of a type of a voice signal input to the pre-processing unit 110 of the disease diagnosis device 100 is described.

Figure 2:
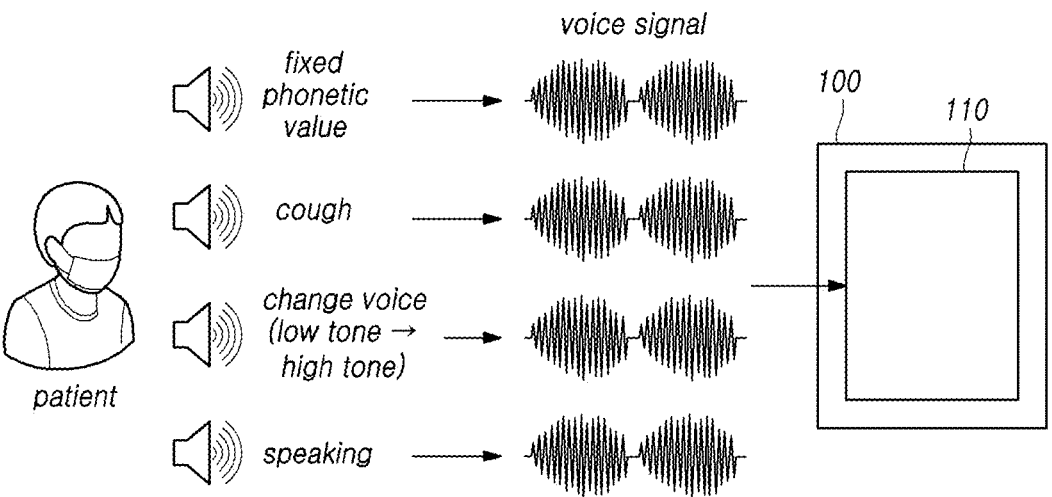
FIG. 2 is a view illustrating an example of a type of a voice signal.

FIG. 2 is a view illustrating an example of a type of a voice signal.

As an example, the type of the above-described voice signal may be any one of 1) a fixed phonetic value signal, 2) a cough signal, 3) a change voice signal, and 4) a speaking signal.

The fixed phonetic value signal is a recorded voice signal of the patient utterance in a fixed phonetic value.

The cough signal is a recorded signal of the patient's coughing.

The change voice signal is a recorded signal of the patient's voice changing from a low-pitched sound having a frequency less than a set threshold frequency to a high-pitched sound having a frequency larger than or equal to the threshold frequency. This is to determine the patient's voice disorder based on the pattern that changes from low tone to high tone.

The speaking signal is a recorded signal of the patient uttering a designated word or sentence (e.g., kanadaramabasa, hello).

In FIG. 1, the type of each of the voice signals VS_1, VS_2, VS_3, ..., VS_N input to the pre-processing unit 110 of the above-described disease diagnosis device 100 may be any one of the fixed phonetic value signal, cough signal, change voice signal, and speaking signal described above. For example, one fixed phonetic value signal, one cough signal, one change voice signal, and one speaking signal may be input to the pre-processing unit 110 of the disease diagnosis device 100.

Hereinafter, an example of the first image signal and the second image signal generated by the pre-processing unit 110 based on the voice signal is described.

For example, the first image signal and the second image signal for the voice signal may be spectrograms for the corresponding voice signal. A spectrogram may be used to visualize a voice signal, and may represent a change in characteristics (e.g., frequency/amplitude) of a voice signal over time.

Figure 3:
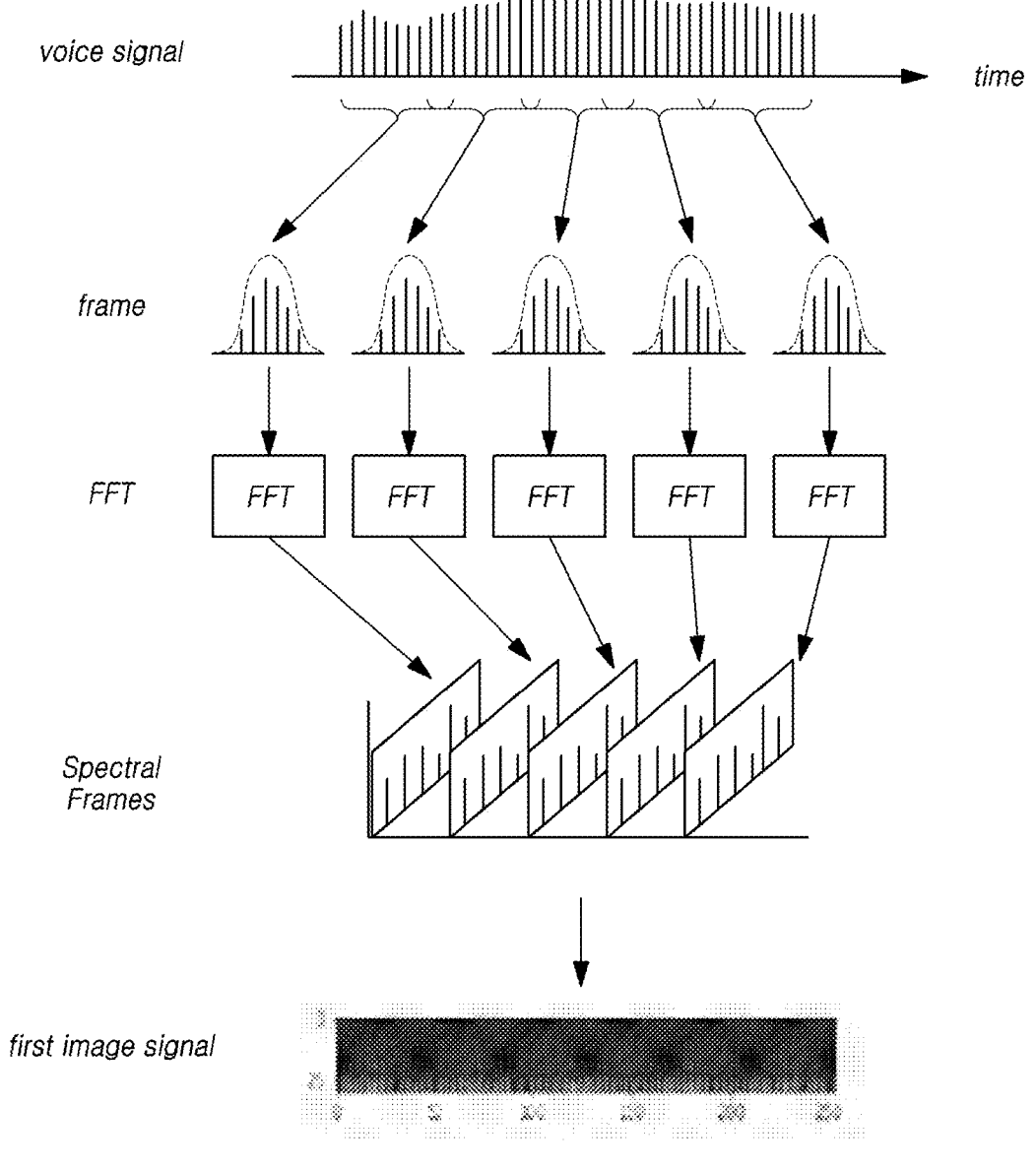
FIG. 3 is a view illustrating an example of generating a first image signal for a voice signal.
Figure 4:
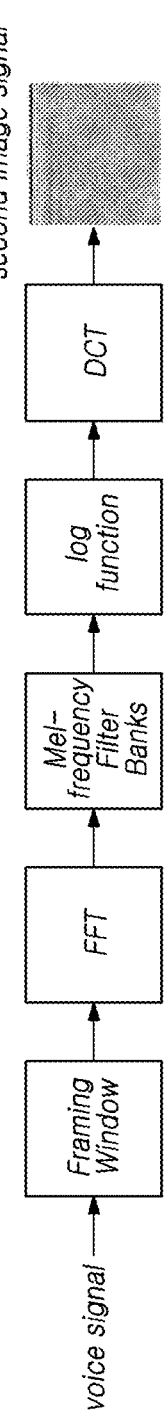
FIG. 4 is a view illustrating an example of generating a second image signal for a voice signal.

Hereinafter, an example of a generation method for generating the first image signal and the second image signal for the voice signal is described. FIG. 3 illustrates a short-time Fourier transform (STFT) method, and FIG. 4 illustrates a mel-frequency cepstral coefficient (MFCC) method.

FIG. 3 is a view illustrating an example of generating a first image signal for a voice signal.

The pre-processing unit 110 may generate a first image signal for the voice signal using a short-time Fourier transform (STFT) method on the voice signal.

In general, to express a frequency component of a voice signal, a fast Fourier transform (FFT) is used. By the FFT, it is possible to visually express how many frequency components a voice signal has. However, since the frequency component expressed by FFT does not show a change in frequency according to the time period, there is a disadvantage in that it is not possible to identify how the frequency is changed in what time period.

Short-time Fourier transform (STFT) is a method for efficiently analyzing a signal whose frequency component changes over time and, in this method, a voice signal is divided according to a plurality of time periods, the frequency component of the voice signal is obtained for each of the divided time periods, and is analyzed.

Referring to FIG. 3, the pre-processing unit 110 may divide the voice signal according to a time period of a specific unit (e.g., 20 ms). In this case, the pre-processing unit 110 may set the divided time periods to overlap each other by a certain ratio (e.g., 50%). For example, the pre-processing unit 110 may divide the time period into a first time period between 0 ms and 20 ms, a second time period between 10 ms and 30 ms, and a third time period between 20 ms and 40 ms from the reference point. In this case, the first time period and the second time period overlap each other by 50%. The second time period and the third time period overlap each other by 50%.

The pre-processing unit 110 may separate the voice signal for each of the divided time periods. As described above, the voice signal divided according to the time period may be referred to as a frame.

The pre-processing unit 110 may generate a spectral frame according to time using FFT for each frame and then combine them to generate a first image signal.

FIG. 4 is a view illustrating an example of generating a second image signal for a voice signal.

The pre-processing unit 110 may generate a second image signal for the voice signal using a mel-frequency cepstral coefficient (MFCC) method on the voice signal.

MFCC is a method for processing a voice signal by applying the characteristic that the human auditory organ is relatively sensitive in a low frequency band, but is relatively insensitive in a high frequency band.

The MFCC method is identical to the STFT method in that it divides a voice signal according to a time period of a specific unit (e.g., 20 ms) and performs an FFT on the voice signal (frame) for each divided time period to generate a frame of a spectrum over time. In this case, as described above, the divided time periods may overlap each other by a certain ratio.

However, the MFCC method is different from the STFT method in that a mel-frequency filter bank based on the mel scale is used for each frame of the spectrum.

The pre-processing unit 110 takes a logarithmic function on the result using the mel-frequency filter bank for each frame of the generated spectrum. The reason why the log function is used is that the human ear does not detect the magnitude of a sound on a linear scale, but detects it close to a log scale.

The pre-processing unit 110 may generate a second image signal for the voice signal by performing discrete cosine transform (DCT) on the result of the above-described log function.

Figure 5:
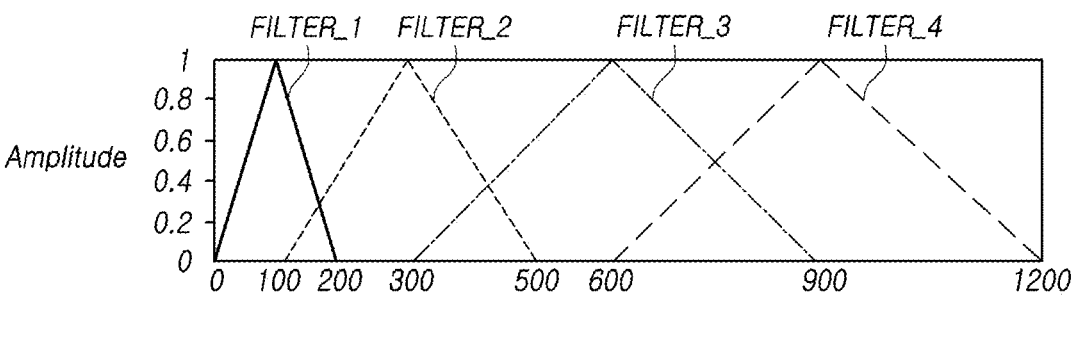
FIG. 5 is a view illustrating an example of the mel-frequency filter bank of FIG. 4.

FIG. 5 is a view illustrating an example of the mel-frequency filter bank of FIG. 4.

The mel-frequency filter bank may include a plurality of mel-frequency filters. In each mel-frequency filter, the amplitude value increases from 0 to 1 from the lowest frequency to the peak frequency, and the amplitude value decreases from 1 to 0 from the peak frequency to the maximum frequency.

For example, in the mel-frequency filter FILTER_1, the amplitude value increases from 0 to 1 from 0 Hz to 100 Hz, and the amplitude value decreases from 1 to 0 from 100 Hz to 200 Hz. In the mel-frequency filter FILTER_2, the amplitude value increases from 0 to 1 from 100 Hz to 300

Hz, and the amplitude value decreases from 1 to 0 from 300 Hz to 500 Hz. In the mel-frequency filter FILTER_3, the amplitude value increases from 0 to 1 from 300 Hz to 600 Hz, and the amplitude value decreases from 1 to 0 from 600 Hz to 900 Hz. In the mel-frequency filter FILTER_4, the amplitude value increases from 0 to 1 from 600 Hz to 900 Hz, and the amplitude value decreases from 1 to 0 from 900 Hz to 1200 Hz.

In the present embodiments, both the first image signal generated by the STFT method and the second image signal generated by the MFCC method may be used to extract the disease probability information. The second image signal generated by the MFCC method has the advantage of reflecting the characteristics of the human auditory organ as compared to the first image signal generated by the STFT method, but since a discrete cosine transformation, which is a linear transformation, is used in the process of converting the voice signal, it has a disadvantage that an element with strong nonlinearity may be removed from the voice signal. Therefore, to reflect both the advantages and disadvantages of the first image signal and the second image signal, the present embodiments may use both the first image signal generated by the STFT method and the second image signal generated by the MFCC method to extract disease probability information.

Figure 6:
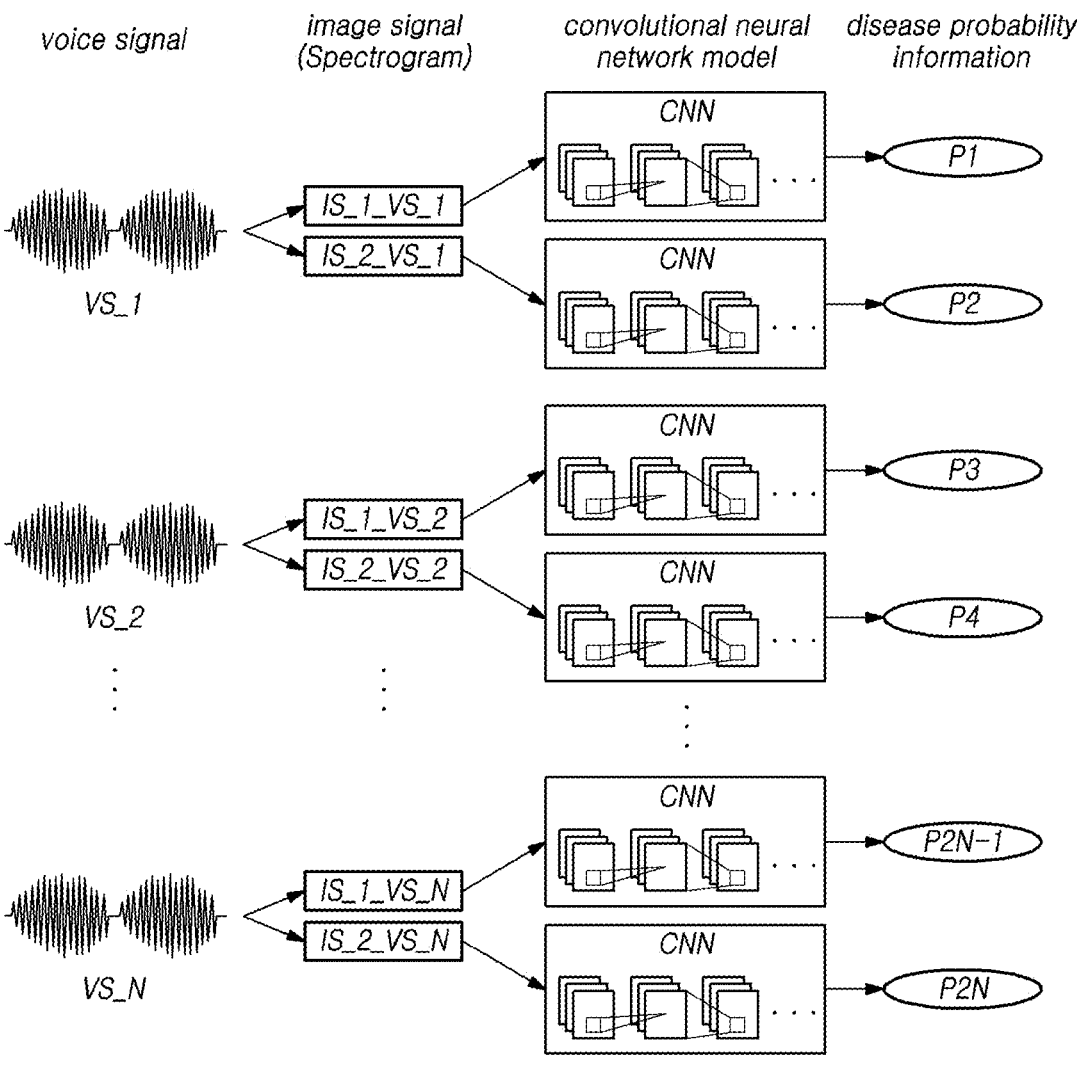
FIG. 6 is a view illustrating an example of an operation in which an extraction unit extracts a plurality of disease probability information.

FIG. 6 is a view illustrating an example of an operation in which an extraction unit extracts a plurality of disease probability information.

In FIG. 6, the artificial intelligence model used by the extraction unit 120 to extract a plurality of disease probability information from the first image signal and the second image signal for each voice signal may be a convolutional neural network (CNN) model. In other words, the extraction unit 120 may extract a plurality of disease probability information by inputting the first image signal and the second image signal for each of the plurality of voice signals to the convolutional neural network determined according to the type of each voice signal and the generation method used to generate each image signal.

The convolutional neural network model may include an input layer, a hidden layer, and an output layer to form a complex mapping function between input values and output values. The complexity may be determined according to the number of hidden layers.

The convolutional neural network model may include one or more convolutional networks. The convolutional network may include one or more convolutional layers and one or more pooling layers as hidden layers. Further, each node of the convolutional network may calculate an output value based on input values from one or more nodes included in the input layer.

Each node in the convolutional network may use the activation function set to compute the output value for the input value. For example, each node in the convolutional network may calculate a value through the weight and bias set for the input value and may compute the output value, using the activation function on the calculated value.

The activation function may be, e.g., a hyperbolic tangent function, a sigmoid function, or a rectified linear unit (ReLU) function.

For optimization, the above-described convolutional neural network model may be trained in a direction that minimizes the error between the calculated result based on the input value and the set reference value (supervised learning data).

In the learning process of the convolutional neural network model, if training using preset training data is excessively performed, the convolutional neural network model shows high accuracy on the training data, but may exhibit low accuracy on new data due to overfitting.

Therefore, the convolutional neural network model may be trained in such a manner as to update the weight used in each node included in the convolutional network of the deep learning model while repeating the process of searching for the minimum error value while reducing the overfitting using, e.g., drop-out, drop-connect, spectral dropout, or regularizer.

Further, the extraction unit 120 may perform normalization by various normalization functions to obtain disease probability information from the result output from the convolutional neural network model. For example, the normalization function may be a softmax function.

In FIG. 6, the extraction unit 120 may determine the disease probability information P1 by inputting the first image signal IS_1_VS_1 for the voice signal VS_1 to the convolutional neural network model and may determine the disease probability information P2 by inputting the second image signal IS_2_VS_1 for the voice signal VS_1 to the convolutional neural network model.

Similarly, the extraction unit 120 may determine the disease probability information P3 by inputting the first image signal IS_1_VS_2 for the voice signal VS_2 to the convolutional neural network model and may determine the disease probability information P4 by inputting the second image signal IS_2_VS_2 for the voice signal VS_2 to the convolutional neural network model. In such a manner, the extraction unit 120 may determine the disease probability information P2N-1 by inputting the first image signal IS_1_VS_N for the voice signal VS_N to the convolutional neural network model and may determine the disease probability information P2N by inputting the second image signal IS_2_VS_N for the voice signal VS_N to the convolutional neural network.

Hereinafter, an operation in which the determining unit 130 determines whether the target disease is negative or positive based on a plurality of disease probability information extracted by the extraction unit 120 is described in this embodiment.

The determining unit 130 may determine a first result value and a second result value based on a plurality of disease probability information and may determine whether the target disease is negative or positive based on the first result value and the second result value.

Figure 7:
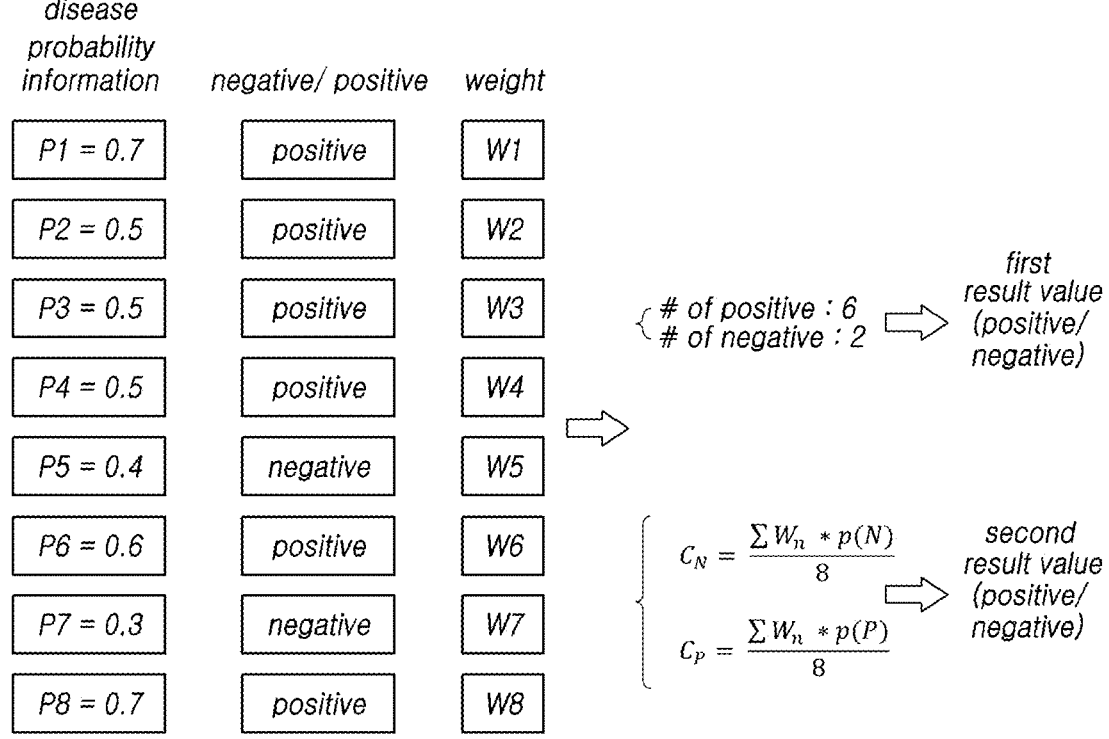
FIG. 7 is a view illustrating an example of an operation for determining a first result value and a second result value based on a plurality of disease probability information.

FIG. 7 is a view illustrating an example of an operation for determining a first result value and a second result value based on a plurality of disease probability information.

In FIG. 7, it is assumed that the determining unit 130 determines a first result value and a second result value based on eight pieces of disease probability information P1, P2, P3, P4, P5, P6, P7, and P8. As an example, the eight pieces of disease probability information P1, P2, P3, P4, P5, P6, P7, and P8 may include 1) the disease probability information extracted from a first image signal and a second image signal generated from a voice signal which is a fixed phonetic value signal, 2) the disease probability information extracted from a first image signal and a second image signal generated from a voice signal which is a cough signal, 3) the disease probability information extracted from a first image signal and a second image signal generated from a voice signal which is a change voice signal, and 4) the disease probability information extracted from a first image signal and a second image signal generated from a voice signal which is a speaking signal. The first image signal generated from each voice signal may be an image signal generated using the STFT method, and the second image signal may be an image signal generated using the MFCC method.

The determining unit 130 may compare the number of disease probability information determined as negative with the number of disease probability information determined as positive among the plurality of disease probability information, and may determine the first result value as negative or positive.

In this case, whether each piece of disease probability information is negative or positive may be determined according to the value of each piece of disease probability information. For example, if the value of the disease probability information is larger than or equal to a set threshold probability value (e.g., 0.5), the determining unit 130 may determine it as positive and, if it is less than the set threshold probability value, determine it as negative.

In FIG. 7, since six pieces of disease probability information P1, P2, P3, P4, P6, and P8 among eight pieces of disease probability information are positive and two pieces of disease probability information P5 and P7 are negative, the determining unit 130 may compare them and determine whether the disease is negative or positive. A specific example of determining the first result value according to the number of disease probability information determined as negative and disease probability information determined as positive is described below with reference to FIG. 8.

The determining unit 130 may determine the second result value as negative or positive civ based on 1) the average value $C_N$ obtained by dividing the total sum of the disease probability information determined as negative, multiplied by the weight corresponding to the artificial intelligence model having generated the disease probability information, by the total number of the disease probability information and 2) the average value $C_P$ obtained by dividing the total sum of the disease probability information determined as positive, multiplied by the weight corresponding to the artificial intelligence model having generated the disease probability information, by the total number of the disease probability information.

The weight multiplied by each disease probability information is a value corresponding to the artificial intelligence model that has generated each disease probability information and may be a value indicating the accuracy of each artificial intelligence model, that is, how accurately the artificial intelligence model determines whether the target disease is positive or negative. For example, the weight W1 multiplied by the disease probability information P1 may be a value indicating the accuracy of the artificial intelligence model that has generated the disease probability information P1. Further, the weight W2 multiplied by the disease probability information P2 may be a value indicating the accuracy of the artificial intelligence model that has generated the disease probability information P2.

In FIG. 7, the above-described $C_N$ may be represented by the following equation.

$$C_N = \frac{\sum W_n * p(N)}{8}$$

p(N) is a value of the disease probability information if the disease probability information is negative and may be determined as 0 if the disease probability information is positive. Since the total number of probability information in FIG. 7 is 8, the denominator of $C_N$ is determined to be 8.

In FIG. 7, the above-described $C_P$ may be represented by the following equation.

$$C_P = \frac{\sum W_n * p(P)}{8}$$

p(P) is a value of the disease probability information if the disease probability information is positive and may be determined as 0 if the disease probability information is negative. Since the total number of probability information in FIG. 7 is 8, the denominator of $C_P$ is determined to be 8.

The determining unit 130 may determine that the second result value is positive if the value of $C_P$ is larger than or equal to $C_N$. In contrast, the determining unit 130 may determine that the second result value is negative if the value of $C_P$ is smaller than $C_N$.

A specific embodiment of determining the second result value using $C_N$, $C_P$ is described with reference to FIG. 9.

FIG. 8 is a view illustrating an example of a first result value according to the number of disease probability information determined as negative and disease probability information determined as positive.

The determining unit 130 may determine that the first result value is positive when the number of disease probability information determined as positive is larger than the number of disease probability information determined as negative. For example, in Case1-1, the determining unit 130 may determine that the first result value is positive when the number of disease probability information determined as positive is six and the number of disease probability information determined as negative is two.

Further, when the number of disease probability information determined as negative is larger than the number of disease probability information determined as positive, the determining unit 130 may determine that the first result value is negative. For example, in Case1-2, if the number of disease probability information determined as positive is three and the number of disease probability information determined as negative is five, the determining unit 130 may determine that the first result value is negative.

Meanwhile, the determining unit 130 may determine that the first result value is positive when the number of disease probability information determined as negative and the number of disease probability information determined as positive are the same. For example, in Case1-3, the determining unit 130 may determine that the first result value is positive when the number of disease probability information determined as positive is four and the number of disease probability information determined as negative is four. This is because when it is unclear whether the target disease is positive or negative, it is necessary to identify whether the target disease is positive or negative through a detailed examination after determining that the disease is positive to prevent such a circumstance where the disease may not be treated due to wrong determination that the target disease is negative although the disease is indeed positive.

The determining unit 130 may determine whether the target disease is negative or positive in various ways according to the first result value and the second result value.

FIG. 9 is a view illustrating an example in which a determining unit determines whether a target disease is negative or positive according to a first result value and a second result value.

In FIG. 9, the determining unit 130 may determine that the target disease is positive when the first result value is positive or the second result value is positive.

In Case 2-1, the determining unit 130 may determine that the first result value is positive when the number of disease probability information determined as positive is six and the number of disease probability information determined as negative is two. Since $C_P$ is 0.8, and $C_N$ is 0.6, the determining unit 130 may determine that the second result value is positive. Since both the first result value and the second result value are positive, the determining unit 130 may determine that the target disease is positive.

In Case 2-2, when the number of disease probability information determined as positive is four and the number of disease probability information determined as negative is four, the determining unit 130 may determine that the first result value is positive since the numbers are the same. Since $C_P$ is 0.6, and $C_N$ is 0.7, the determining unit 130 may determine that the second result value is negative. Since the first result value is positive, the determining unit 130 may determine that the target disease is positive.

In Case 2-3, the determining unit 130 may determine that the first result value is negative since the number of disease probability information determined as positive is three and the number of disease probability information determined as negative is five. Since $C_P$ is 0.7, and $C_N$ is 0.6, the determining unit 130 may determine that the second result value is positive. Since the second result value is positive, the determining unit 130 may determine that the target disease is positive.

In Case 2-4, the determining unit 130 may determine that the first result value is negative since the number of disease probability information determined as positive is three and the number of disease probability information determined as negative is five. Since $C_P$ is 0.6, and $C_N$ is 0.7, the determining unit 130 may determine that the second result value is negative. Since both the first result value and the second result value are negative, the determining unit 130 may determine that the target disease is negative.

FIG. 10 is a view illustrating another example in which a determining unit determines whether a target disease is negative or positive according to a first result value and a second result value.

In FIG. 10, the determining unit 130 may determine whether a target disease where a weight higher than that of the first result value is applied to the second result value is negative or positive. The reason why a weight higher than that of the first result value is applied to the second result value is that the second result value considers the characteristics (e.g., accuracy) of the artificial intelligence model in the process of determining each piece of disease probability information.

In the above-described Case 2-2, the determining unit 130 may determine that the first result value is positive and the second result value is negative. In this case, in FIG. 9, the determining unit 130 determines that the target disease is positive because the first result value is positive, but in FIG. 10, the determining unit 130 determines that the target disease is negative because the second result value to which the higher weight is applied is negative.

Figure 11:
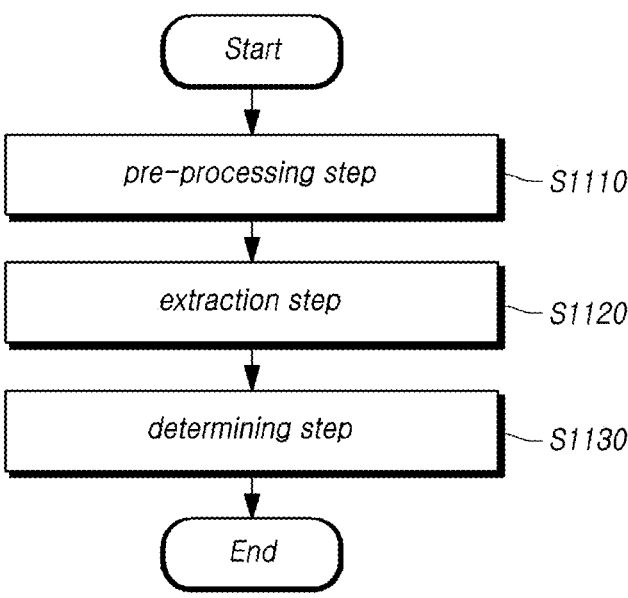
FIG. 11 is a flowchart illustrating a disease diagnosis method according to an embodiment.

FIG. 11 is a flowchart illustrating a disease diagnosis method according to an embodiment.

Referring to FIG. 11, a disease diagnosis method may include a pre-processing step S1110, an extraction step S1120, and a determining step S1130.

The pre-processing step S1110 may receive a plurality of voice signals and generate a first image signal and a second image signal for each voice signal. In this case, the type of each voice signal may be any one of a fixed phonetic value signal, a cough signal, a change voice signal, and a speaking signal described above in connection with FIG. 2.

The first image signal and the second image signal for each voice signal may be spectrograms for each voice signal. For example, the pre-processing step S1110 may generate a first image signal for each voice signal using a short-time Fourier transform (STFT) method for each voice signal and generate a second image signal for each voice signal using a mel-frequency cepstral coefficient (MFCC) method for each voice signal.

The extraction step S1120 may extract a plurality of disease probability information for the target disease causing a voice change using the artificial intelligence model determined according to the type of each voice signal and the generation method used to generate each image signal for the first image signal and the second image signal for each voice signal generated in the pre-processing step S1110.

In this case, the artificial intelligence model may be a convolutional neural network model. In other words, the extraction step S1120 may extract a plurality of disease probability information by inputting the first image signal and the second image signal for each voice signal to the convolutional neural network determined according to the type of each voice signal and the generation method used to generate each image signal.

The determining step S1130 may determine whether the target disease is negative or positive based on the plurality of disease probability information extracted in the extraction step S1120.

The determining step S1130 may compare the number of disease probability information determined as negative with the number of disease probability information determined as positive among the plurality of disease probability information, and may determine the first result value as negative or positive.

The determining step S1130 may determine the second result value as negative or positive based on 1) the average value obtained by dividing the total sum of the disease probability information determined as negative among the plurality of disease probability information, multiplied by the weight corresponding to the artificial intelligence model having generated the disease probability information, by the total number of the disease probability information and 2) the average value obtained by dividing the total sum of the disease probability information determined as positive among the plurality of disease probability information, multiplied by the weight corresponding to the artificial intelligence model having generated the disease probability information, by the total number of the disease probability information.

The determining step S1130 may determine whether the disease is negative or positive based on the first result value and the second result value.

The determining step S1130 may determine that the first result value is positive if the number of disease probability information determined as negative among the plurality of disease probability information is identical to the number of disease probability information determined as positive.

The determining step S1130 may determine that the target disease is positive if the first result value is positive or the second result value is positive.

The above-described disease diagnosis device 100 may be implemented by a computing device including at least some of a processor, a memory, a user input device, and a presentation device. The memory is a medium that stores computer-readable software, applications, program modules, routines, instructions, and/or data, coded to perform specific tasks when executed by a processor. The processor may read and execute the computer-readable software, applications, program modules, routines, instructions, and/or data stored in the memory. The user input device may be a means for allowing the user to input a command to the processor to execute a specific task or to input data required for the execution of the specific task. The user input device may include a physical or virtual keyboard or keypad, key button, mouse, joystick, trackball, touch-sensitive input means, or a microphone. The presentation device may include, e.g., a display, a printer, a speaker, or a vibrator.

The computing device may include various devices, such as smartphones, tablets, laptops, desktops, servers, clients, and the like. The computing device may be a single stand-alone device and may include a plurality of computing devices operating in a distributed environment composed of a plurality of computing devices cooperating with each other through a communication network.

Further, the above-described disease diagnosis method may be executed by a computing device that includes a processor and a memory storing computer readable software, applications, program modules, routines, instructions, and/or data structures, coded to perform an image diagnosis method utilizing a deep learning model when executed by the processor.

The present embodiments described above may be implemented through various means. For example, the present embodiments may be implemented by various means, e.g., hardware, firmware, software, or a combination thereof.

When implemented in hardware, the image diagnosis method using a deep learning model according to the present embodiments may be implemented by, e.g., one or more application specific integrated circuits (ASICs), digital signal processors (DSPs), digital signal processing devices (DSPDs), programmable logic devices (PLDs), field programmable gate arrays (FPGAs), processors, controllers, micro-controllers, or micro-processors.

For example, the disease diagnosis method according to embodiments may be implemented by an artificial intelligence semiconductor device in which neurons and synapses of the deep neural network are implemented with semiconductor devices. In this case, the semiconductor devices may be currently available semiconductor devices, e.g., SRAM, DRAM, or NAND or may be next-generation semiconductor devices, such as RRAM, STT MRAM, or PRAM, or may be combinations thereof.

When the disease diagnosis method according to embodiments is implemented using an artificial intelligence semiconductor device, the results (weights) of training the deep learning model with software may be transferred to synaptic mimic devices disposed in an array, or learning may be performed in the artificial intelligence semiconductor device.

When implemented in firmware or hardware, the disease diagnosis method according to the present embodiments may be implemented in the form of a device, procedure, or function performing the above-described functions or operations. The software code may be stored in a memory unit and driven by a processor. The memory unit may be positioned inside or outside the processor to exchange data with the processor by various known means.

The above-described terms, such as "system," "processor," "controller," "component," "module," "interface," "model," or "unit," described above may generally refer to computer-related entity hardware, a combination of hardware and software, software, or software being executed. For example, the above-described components may be, but are not limited to, processes driven by a processor, processors, controllers, control processors, entities, execution threads, programs, and/or computers. For example, both an application being executed by a controller or a processor and the controller or the processor may be the components. One or more components may reside within a process and/or thread of execution, and the components may be positioned in one device (e.g., a system, a computing device, etc.) or distributed in two or more devices.

Meanwhile, another embodiment provides a computer program stored in a computer recording medium for performing the above-described disease diagnosis method. Further, another embodiment provides a computer-readable recording medium storing a program for realizing the above-described disease diagnosis method.

The program recorded on the recording medium may be read, installed, and executed by a computer to execute the above-described steps.

As such, for the computer to read the program recorded on the recording medium and execute the implemented functions with the program, the above-described program may include code coded in a computer language, such as C, C++, JAVA, or machine language, which the processor (CPU) of the computer may read through a computer device interface.

Such code may include a function code related to a function defining the above-described functions or may include an execution procedure-related control code necessary for the processor of the computer to execute the above-described functions according to a predetermined procedure.

Further, the code may further include additional information necessary for the processor of the computer to execute the above-described functions or memory reference-related code as to the position (or address) in the internal or external memory of the computer the media should reference.

Further, when the processor of the computer needs to communicate with, e.g., another computer or a server at a remote site to execute the above-described functions, the code may further include communication-related code as to how the processor of the computer should communicate with the remote computer or server using the communication module of the computer and what information or media should be transmitted/received upon communication.

The above-described computer-readable recording medium may include, e.g., ROMs, RAMs, CD-ROMs, magnetic tapes, floppy disks, or optical data storage devices, or may also include carrier wave-type implementations (e.g., transmissions through the Internet).

Further, the computer-readable recording medium may be distributed to computer systems connected via a network, and computer-readable codes may be stored and executed in a distributed manner.

The functional programs for implementing the present invention and code and code segments related thereto may easily be inferred or changed by programmers of the technical field to which the present invention pertains, considering, e.g., the system environments of the computer reading and executing the program.

The disease diagnosis method described in connection with FIG. 10 may be implemented in the form of recording media including computer-executable instructions, such as application or program modules. The computer-readable medium may be an available medium that is accessible by a computer. The computer-readable storage medium may include a volatile medium, a non-volatile medium, a separable medium, and/or an inseparable medium. The computer-readable medium may include a computer storage medium. The computer storage medium may include a volatile medium, a non-volatile medium, a separable medium, and/or an inseparable medium that is implemented in any method or scheme to store computer-readable commands, data architecture, program modules, or other data or information.

The above-described disease diagnosis method may be executed by an application installed on a terminal, including a platform equipped in the terminal or a program included in the operating system of the terminal), or may be executed by an application (or program) installed by the user on a master terminal via an application providing server, such as a web server, associated with the service or method, an application, or an application store server. In such a sense, the above-described disease diagnosis method may be implemented in an application or program installed as default on the terminal or installed directly by the user and may be recorded in a recording medium or storage medium readable by a terminal or computer.

Although embodiments of the present invention have been described with reference to the accompanying drawings, It will be appreciated by one of ordinary skill in the art that the present disclosure may be implemented in other various specific forms without changing the essence or technical spirit of the present disclosure. Thus, it should be noted that the above-described embodiments are provided as examples and should not be interpreted as limiting. Each of the components may be separated into two or more units or modules to perform its function(s) or operation(s), and two or more of the components may be integrated into a single unit or module to perform their functions or operations.

It should be noted that the scope of the present invention is defined by the appended claims rather than the described description of the embodiments and include all modifications or changes made to the claims or equivalents of the claims.

The invention claimed is:

1. A disease diagnosis device, comprising:
   a pre-processing unit configured to receive N (N is a number greater than or equal to 2) voice signals and generating 2N image signals including N first image signals and N second image signals that are image signals for each voice signal;
   an extraction unit configured to extract 2N disease probability information for a target disease causing a voice change using K*L (each of K and L is a number greater than or equal to 2) convolutional neural network (CNN) models determined according to K types of each voice signal and L generation methods used to generate each image signal for N first image signals and N second image signals for each voice signal; and
   a determining unit configured to determine whether the target disease is negative or positive based on the 2N number of disease probability information, wherein the determining unit is configured to compare the number of disease probability information determined as negative with the number of disease probability information determined as positive among the plurality of disease probability information and determines a first result value as negative or positive,
   determines a second result value as negative or positive based on 1) the average value obtained by dividing the total sum of the disease probability information determined as negative among the plurality of disease probability information, multiplied by a weight corresponding to the artificial intelligence model having generated the disease probability information, by the total number of the disease probability information and 2) the average value obtained by dividing the total sum of the disease probability information determined as positive among the plurality of disease probability information, multiplied by the weight corresponding to the artificial intelligence model having generated the disease probability information, by the total number of the disease probability information, and determines whether the target disease is negative or positive based on the first result value and the second result value, wherein the each voice signal is a signal recorded from a patient through a device capable of recording voice, and the format of each of the voice signals is one of wav, mp3, nsp, mp4, and avi, wherein the first image signal and the second image signal for each voice signal are spectrograms representing a change in the characteristics of each voice signal over time, wherein the pre-processing unit generates a first image signal for each voice signal using a short-time Fourier transform (STFT) method that divides the voice signal into a plurality of frames according to a time period of a specific unit, then performs a fast Fourier transform (FFT) on each frame for each divided time period to generate a frame of a spectrum over time, and then combines these frames to generate the first image signal on each voice signal and generates a second image signal for each voice signal using a mel-frequency cepstral coefficient (MFCC) method that divides the voice signal into a plurality of frames according to a time period of a specific unit, then performs the FFT on each frame for each divided time period to generate a frame of a spectrum over time, applies a logarithmic function to the result of each frame of the spectrum using a Mel-frequency filter bank and then performs a discrete cosine transform (CDCT) on the result of the logarithmic function to generate the second image signal on each voice signal, wherein each of the convolutional neural network (CNN) models includes an input layer, one or more hidden layers, and an output layer to form a complex mapping function between input values and output values, each of the one or more hidden layers includes one or more convolutional layers and one or more pooling layers, and each node of the hidden layer computes a value through weights and biases set for the input value and computes an output value, using an activation function on the calculated value, and wherein each of the convolutional neural network (CNN) models is trained in a direction that minimizes the error between the calculated result based on the input value and the set reference value.

2. The disease diagnosis device of claim 1, wherein the type of each voice signal is any one of a fixed phonetic value signal, a cough signal, a change voice signal changing from a low tone to a high tone, and a speaking signal.

3. The disease diagnosis device of claim 1, wherein the determining unit determines that the first result value is positive if the number of disease probability information determined as negative among the plurality of disease probability information is identical to the number of disease probability information determined as positive.

4. The disease diagnosis device of claim 1, wherein the determining unit determines that the target disease is positive if the first result value is positive or the second result value is positive.

5. The disease diagnosis device of claim 1, wherein the determining unit determines whether the target disease is negative or positive by applying a weight higher than that of the first result value to the second result value.

* * * * *